United States Patent [19]

Ueda et al.

[11] Patent Number: 4,725,306

[45] Date of Patent: Feb. 16, 1988

[54] PYRIDINECARBOXAMIDE PLANT GROWTH INHIBITORS

[75] Inventors: Yoichiro Ueda, Himeji; Yoshiyuki Hirako, Otake; Kazuhisa Masamoto, Himeji; Yukihisa Goto, Himeji; Hiroshi Yagihara, Himeji; Yasuo Morishima, Kobe; Hirokazu Osabe, Himeji, all of Japan

[73] Assignee: Daicel Chemical Industries Ltd., Osaka, Japan

[21] Appl. No.: 789,411

[22] Filed: Oct. 21, 1985

[30] Foreign Application Priority Data

Nov. 9, 1984 [JP] Japan .................. 59-237100
Jan. 10, 1985 [JP] Japan .................. 60-2719

[51] Int. Cl.$^4$ .................. A01N 43/40; C07D 213/82; C07D 401/06; C07D 405/06
[52] U.S. Cl. .................. 71/94; 71/90; 546/261; 546/284; 546/291
[58] Field of Search .................. 546/291, 261, 284; 71/94, 90

[56] References Cited

FOREIGN PATENT DOCUMENTS 1115278 12/1981 Canada .................. 546/291

Primary Examiner—Alan L. Rotman
Assistant Examiner—Dale A. Bjorkman
Attorney, Agent, or Firm—Stiefel, Gross & Kurland

[57] ABSTRACT

Novel pyridinecarboxamide compounds having the general formula (I)

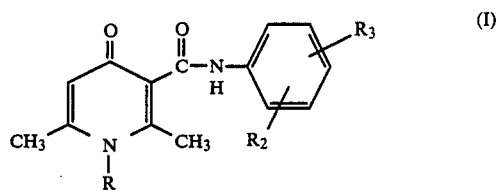

or salts thereof wherein R is alkoxy group, aralkyloxy group or a group of —$(CH_2)_n$—$R_1$ wherein n is an integer from 1 to 3 and $R_1$ is hydroxy group, lower alkoxy group, mercapto group, lower alkylthio group, amino group, di-lower alkylamino group, $C_{3-11}$ alkyl group, lower alkenyl group, lower alkynyl group, cycloalkyl group, 5- or 6-membered heterocyclic group, or aryl group substituted by one or two substituents of halogen, lower alkyl or lower alkoxy; $R_2$ and $R_3$ bond at the 3,4 or 5 position of benzene ring and are, the same or different, hydrogen atom, halogen atom, cyano group, nitro group, amino group, lower alkyl group, halogenated lower alkyl group, hydroxy group, lower alkoxy group, aryloxy group, carboxy group or lower alkoxycarbonyl group, which possess plant growth inhibitory activities and also antiinflammatory activity.

8 Claims, No Drawings

PYRIDINECARBOXAMIDE PLANT GROWTH INHIBITORS

BACKGROUND OF THE INVENTION

1. Field of the Invention

This invention relates to novel compounds which belong to 1,4-dihydro-2,6-dimethyl-4-oxo-3-pyridinecarboxamides. The compounds of this invention show growth inhibitory activities on plants and also anti-inflammatory activity.

2. Description of the Prior Arts

Some compounds belonging to 1,4-dihydro-2,6-dimethyl-4-oxo-3-pyridinecarboxamides are found in literature. In Yakagukuzassi, 101, 40 (1981), Kato et al. reported on four compounds, namely N-(4-chlorophenyl)-1,4-dihydro-2,6-dimethyl-4-oxo-3-pyridinecarboxamide, 1,4-dihydro-2,6-dimethyl-4-oxo-N-phenyl-1-(phenylmethyl)-3-pyridinecarboxamide, 1,4-dihydro-N-(4-methoxyphenyl)-2,6-dimethyl-4-oxo-1-(phenylmethyl)-3-pyridinecarboxamide and N-(4-chlorophenyl)-1,4-dihydro-2,6-dimethyl-4-oxo-1-(phenylmethyl)-3-pyridinecarboxamide, as one of the studies on reactivity of ketene derivatives, but they did not refer to utility thereof. In Canadian Pat. No. 1,115,278 [and also J. B. Pierce et al, J. Med. Chem. 25, 131 (1982)], there are disclosed 4-pyridone compounds possessing anti-inflammatory activity, i.e., 1,4-dihydro-2,6-dimethyl-4-oxo-N,1-diphenyl-3-pyridinecarboxamide, N,1-dibutyl-1,4-dihydro-2,6-dimethyl-4-oxo-3-pyridinecarboxamide, N,1-didodecyl-1,4-dihydro-2,6-dimethyl-4-oxo-3-pyridinecarboxamide, N-(4-chlorophenyl)-1-ethyl-1,4-dihydro-2,6-dimethyl-4-oxo-3-pyridinecarboxamide, etc.

On the other hand, 1,4-dihydro-4-oxo-3-pyridinecarboxylic acid derivatives as compounds which show plant growth regulating activity, especially chemical hybridizing activity, are known in Japanese Patent Unexamined Publication Nos. Sho 52(1977)-144,676 (see also U.S. Pat. No. 4,051,142) and Sho 57(1982)-114,573 (see also E.P. No. 40,082). However, plant growth inhibitory agents whose active ingredients are 1,4-dihydro-2,6-dimethyl-4-oxo-3-pyridinecarboxamides as in the formula (I) shown below are not known.

SUMMARY OF THE INVENTION

This invention provides compounds of the formula (I) and salts thereof.

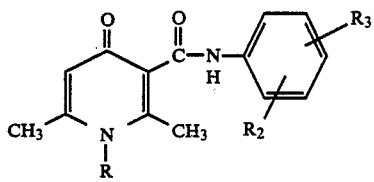

(I)

In the formula (I), R is alkoxy group, aralkyloxy group or a group of —(CH$_2$)$_n$—R$_1$ wherein n is an integer from 1 to 3 and R$_1$ is hydroxy group, lower alkoxy group, mercapto group, lower alkylthio group, amine group, di-lower alkylamino group, C$_{3-11}$ alkyl group, lower alkenyl group, lower alkynyl group, cycloalkyl group, 5- or 6-membered heterocyclic group, or aryl group substituted by one or two substituents of halogen, lower alkyl or lower alkoxy; R$_2$ and R$_3$ bond at the 3, 4 or 5 positions of benzene ring and are, the same or different, hydrogen atom, halogen atom, cyano group, nitro group, amino group, lower alkyl group, halogenated lower alkyl group, hydroxy group, lower alkoxy group, aryloxy group, carboxy group or lower alkoxycarbonyl group.

DESCRIPTION OF PREFERRED EMBODIMENTS

The term "lower" used for lower alkyl, lower alkoxy or like group in this invention means a group containing 1–5 carbon atoms. Specifically, there may be mentioned as lower alkyl group methyl, ethyl, propyl, isopropyl, butyl, isobutyl, pentyl or isopentyl; as lower alkoxy group methoxy, ethoxy, propoxy, isopropoxy or butoxy; as lower alkoxycarbonyl group methoxycarbonyl, ethoxycarbonyl, propoxycarbonyl or butoxycarbonyl; or as lower alkylthio group methylthio, ethylthio, propylthio, isopropylthio, butylthio or pentylthio. As lower alkenyl or lower alkynyl group may be mentioned vinyl, allyl, isopropenyl, 2-butenyl, 1,3-butadienyl, 2-pentenyl, 1,4-pentadienyl, 1,6-heptadienyl, 1-hexenyl, ethynyl or 2-propynyl.

Examples of alkoxy and aralkyloxy group as used in the definition of R include alkoxy groups containing 1–12 carbon atoms such as methoxy, ethoxy, propoxy, isopropoxy, butoxy, isobutoxy, pentyloxy, 2-methylbutoxy, hexyloxy, 2 (or 3)-methylpentyloxy, octyloxy, nonyloxy, decyloxy, dodecyloxy; aralkyloxy groups such as phenylmethoxy, phenethyloxy, phenylpropoxy or phenylbutoxy group which may be substituted by an alkyl or a halogen atom at the aryl ring.

Examples of cycloalkyl group include cyclopropyl, cyclopentyl and cyclohexyl.

Examples of the aryl group include substituted phenyl and substituted naphthyl. The substituents here include halogen atom, lower alkyl group and/or lower alkoxy group.

Halogen atom includes chlorine, bromine and fluorine atom.

5- or 6-membered heterocyclic group includes 5- or 6-membered rings containing one to three hetero atoms selected from nitrogen atom, oxygen atom and sulfur atom. The examples of the 5-membered heterocyclic group are furyl, tetrahydrofuryl, thienyl, thiazolyl, isothiazolyl, oxazolyl, isooxazolyl or pyrazolyl and the 6-membered heterocyclic group pyridyl, pyrimidinyl, pyrazinyl or pyridazinyl. These heterocyclic groups may be substituted by alkyl as methyl or ethyl, halogen atom or phenyl. When the heterocyclic group is substituted by phenyl, it may form a condensed ring combining the two adjacent carbon atoms in the heterocyclic group with phenyl group. Examples of the condensed ring are benzothiazolyl, benzofuryl, guinazolinyl or quinoxalinyl group.

The compound of the formula (I) in this invention may form an addition salt with an acid such as hydrochloric acid, sulfuric acid, phosphoric acid, methanesulfonic acid, p-toluenesulfonic acid or trifluoroacetic acid when sufficiently basic, and also form a salt with an inorganic base when it contains a carboxylic group. Such salts are also included in this invention.

The compound of the formula (I) in this invention may be prepared by any of the following methods.

Method A

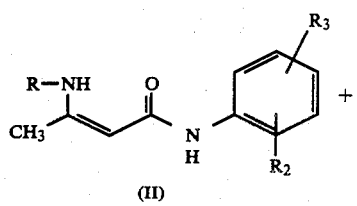

(II)

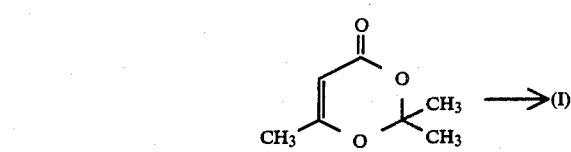

[R, $R_2$ and $R_3$ of the formula (II) are the same as those in the formula (I).]

This method comprises reacting a 3-aminocrotonic acid anilide derivative (II) or its tautomer with 2,2,6-trimethyl-4H-1,3-dioxin-4-one in an appropriate solvent (e.g., toluene or xylene) under heating at a temperature of e.g., 100° C.–140° C. 2-Ethyl-2,6-dimethyl-4H-1,3-dioxin-4-one is also useful in place of 2,2,6-trimethyl-4H-1,3-dioxin-4-one. Also, in this method, 3-aminocrotonic acid anilide derivative (II) is not necessarily required to be in its isolated form but may be in the form of the crude reaction mixture of an amine of the formula (III) with a compound of the formula (IV)

RNH$_2$    (III)

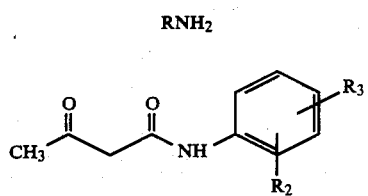

[R, $R_2$ and $R_3$ in the formula (II) and (IV) are the same as those in the formula (I).] For the practical purpose it is convenient to use the crude reaction mixture as such.

(Method B)

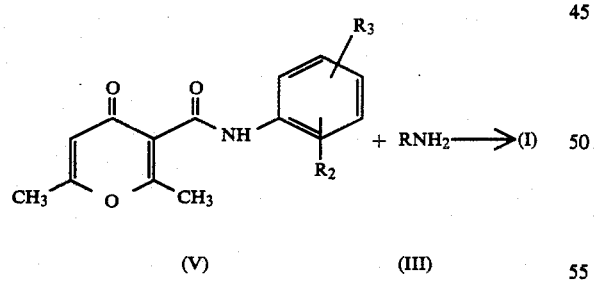

[R, $R_2$ and $R_3$ in the formula (III) and (V) are the same as those in the formula (I).]

This method comprises reacting a 4-pyrone compound (V) corresponding to the formula (I), i.e., 2,6-dimethyl-4-oxo-N-phenyl-4H-pyran-3-carboxamide with an amine of the formula (III) or a salt thereof in an appropriate solvent (e.g., ethanol or water) at a temperature from room temperature to about 60° C. The amount of the amine employed is equimolecular or more to the 4-pyrone compound or a large excess if needed. When the amine is used as its available salt, it is required to convert to its free form by addition of an organic or an inorganic base in an amount needed for neutralization or more.

(Method C)

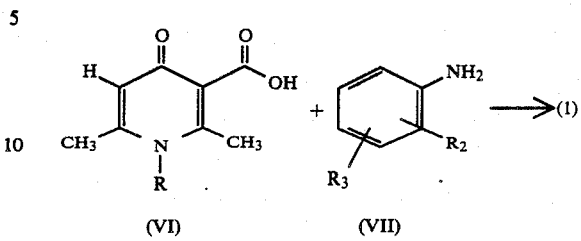

[R, $R_2$ and $R_3$ in the formula (VI) and (VII) are the same as those in the formula (I).]

This method comprises reacting a carboxylic acid corresponding to the formula (I), i.e., 1,4-dihydro-2,6-dimethyl-4-oxo-3-pyridinecarboxylic acid derivative (VI) with an aniline derivative (VII) in the presence of a condensing agent for dehydration. It is advantageous to use as the condensing agent for dehydration 1-substituted-2-halopyridinium salt and a tertiary amine according to the method described in e.g. Japanese Patent Unexamined Publication No. Sho 52(1977)-57102.

This invention is illustrated further by examples hereinafter. Also, growth-inhibitory activities on plants of the compounds of the invention are shown in reference examples.

Furthermore, a related specific compound in addition to the compounds shown in the examples is as follows; 1-butyl-1,4-dihydro-2,6-dimethyl-N-(3,5-dimethylphenyl)-4-oxo-3-pyridinecarboxamide.

EXAMPLE 1

1-(4-fluorophenylmethyl)-1,4-dihydro-2,6-dimethyl-4-oxo-N-phenyl-3-pyridinecarboxamide

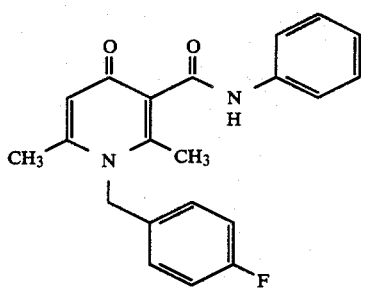

(Method A)

A mixture of 2.53 g (14.3 m mol) of acetoacetanilide, 1.79 g (14.3 m mol) of 4-fluorobenzylamine and 20 ml of toluene was refluxed for 1.5 hours, while the resulting water was removed through a Dean-Stark's water-separator, together with about 6 ml of toluene. To the mixture was dropwise added a solution of 5.10 g (35.8 m mol) of 2,2,6-trimethyl-4H-1,3-dioxin-4-one in 10 ml of toluene within about 30 minutes. After refluxing for further 20 minutes, the reaction temperature was cooled at room temperature to precipitate crystals of the title compound. The crystals separated by filtration were dried under vacuo to afford 2.04 g of the product having mp. 186°–188° C.

EXAMPLE 2

N-(4-chlorophenyl)-1,4-dihydro-1-(3-methoxypropyl)-2,6-dimethyl-4-oxo-3-pyridinecarboxamide

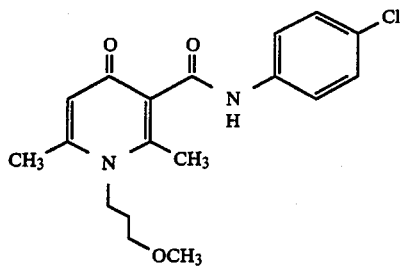

(Method B)

To a solution of 2.78 g (10.0 m mol) of N-(4-chlorophenyl)-2,6-dimethyl-4-oxo-4H-pyran-3-carboxamide (mp. 201°-202° C.) in 50 ml of ethanol and 10 ml of water was added 0.98 g (11.0 m mol) of 3-methoxypropylamine and 0.7 g of sodium carbonate, and the mixture was stirred for 5 hours at room temperature. The reaction mixture was then concentrated under vacuo. The residue was dissolved in 100 ml of ethyl acetate and the solution was washed with water, and then with saturated sodium bicarbonate solution. The organic layer was dried and concentrated in an usual manner and the residue was recrystallized from ethyl acetate to afford 3.13 g (yield: 79%) of the title compound having mp. 164°-166.5° C.

EXAMPLE 3

1-(4-chlorophenylmethyl)-1,4-dihydro-2,6-dimethyl-4-oxo-N-phenyl-3-pyridinecarboxamide

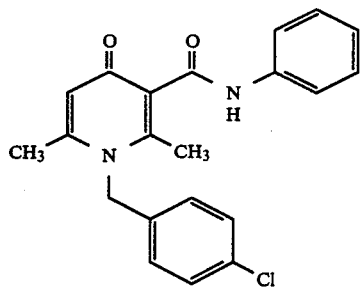

(Method C)

A mixture of 2.92 g (10.0 m mol) of 1-(4-chlorophenylmethyl)-1,4-dihydro-2,6-dimethyl-4-oxo-3-pyridinecarboxylic acid and 3.60 g (12 m mol) of 2-chloro-1-methyl-pyridinium tosylate dissolved in 100 ml of chloroform was treated with 2.43 g (24 m mol) of triethylamine and stirred for 30 minutes at room temperature. Aniline (0.93 g, 10 m mol) was added to the reaction mixture followed by stirring for 4 hours at room temperature. The reaction mixture, transferred to a separatory funnel, was washed with a saturated sodium bicarbonate solution. The organic layer was dried and concentrated in an usual manner to give 4.5 g of an oily residue. The residue was dissolved in 20 ml of hot toluene and cooled to room temperature to afford 1.17 g of the title compound having mp. 246°-248° C.

The following Table 1 and Table 2 show physical properties of the compounds associated with this invention. Numbers in the column "Evaluation" in Table 2 were obtained as follows.

A carrier was prepared by mixing 50 parts (by weight) of talc, 25 parts of bentonite, 2 parts of Solpole-9047 (Toho Chemical Co., Ltd, Japan) and 3 parts of Solpole-5039 (Toho Chemical Co., Ltd, Japan). 50 parts of a test compound and 200 parts of the carrier was mixed to obtain 20% wettable powder, followed by dispersing the powder in distilled water to make a dispersion of the definite concentrations.

Seeds of Oryza sativa L., Echinochloa crus-galli L., and Raphanus sativus L. were germinated in a laboratory dish, to which the dispersion was added. After breeding for 7 days in a thermostatic box kept at 25° C. under illumination of fluorescent tubes, growth of plant was observed. In the column of "Evaluation" of Table 2, the designation 1 denotes no influence, 2 denotes 25% growth inhibition, 3 denotes 50% growth inhibition, 4 denotes 75% growth inhibition and 5 denotes 100% growth inhibition.

TABLE 1

| Example No. | R | $R_2$ | $R_3$ | Method | Melting Point (°C.) | Molecular Formula |
|---|---|---|---|---|---|---|
| 1 | 4-fluorophenylmethyl | H | H | A | 186–188 | $C_{21}H_{19}FN_2O_2$ |
| 2 | 4-chlorophenylmethyl | H | H | C | 246–248 | $C_{21}H_{19}ClN_2O_2$ |
| 3 | butyl | H | H | A | 146.5–148.5 | $C_{18}H_{22}N_2O_2$ |
| 4 | hexyl | H | H | A | 138–140 | $C_{20}H_{26}N_2O_2$ |
| 5 | cyclohexylmethyl | H | H | A | 151–153 | $C_{21}H_{26}N_2O_2$ |
| 6 | allyl | H | H | A | 132–132.5 | $C_{17}H_{18}N_2O_2$ |
| 7 | 2-fluorophenylmethyl | H | H | A | 211–213 | $C_{21}H_{19}FN_2O_2$ |
| 8 | 2-chlorophenylmethyl | H | H | C | 205–207.5 | $C_{21}H_{19}ClN_2O_2$ |
| 9 | 3-chlorophenylmethyl | H | H | A | 172–173 | $C_{21}H_{19}ClN_2O_2$ |
| 10 | 2,4-dichlorophenylmethyl | H | H | A | 229–231 | $C_{21}H_{18}Cl_2N_2O_2$ |
| 11 | 3,4-dichlorophenylmethyl | H | H | A | 207.5–209 | $C_{21}H_{18}Cl_2N_2O_2$ |
| 12 | 2-methoxyphenylmethyl | H | H | A | 226–229 | $C_{22}H_{22}N_2O_3$ |
| 13 | 3-methoxyphenylmethyl | H | H | A | 172–175 | $C_{22}H_{22}N_2O_3$ |
| 14 | 4-methoxyphenylmethyl | H | H | A | 200–201.5 | $C_{22}H_{22}N_2O_3$ |
| 15 | 3-methylphenylmethyl | H | H | A | 161–163.5 | $C_{22}H_{22}N_2O_2$ |
| 16 | 4-methylphenylmethyl | H | H | A | 204–207 | $C_{22}H_{22}N_2O_2$ |
| 17 | 4-isopropylphenylmethyl | H | H | A | 237.5–239 | $C_{24}H_{26}N_2O_2$ |
| 18 | 4-t-butylphenylmethyl | H | H | A | 238–239 | $C_{25}H_{28}N_2O_2$ |

TABLE 1-continued

| Example No. | R | $R_2$ | $R_3$ | Method | Melting Point (°C.) | Molecular Formula |
|---|---|---|---|---|---|---|
| 19 | 2-furylmethyl | H | H | A | 190-193 | $C_{19}H_{18}N_2O_3$ |
| 20* | 2-pyridylmethyl | H | H | A | 201-205.5 | $C_{21}H_{23}N_3O_3$ |
| 21 | 3-pyridylmethyl | H | H | A | 188-190 | $C_{20}H_{19}N_3O_2$ |
| 22 | 4-pyridylmethyl | H | H | A | 192.5-197 | $C_{20}H_{19}N_3O_2$ |
| 23 | 2-methoxyethyl | H | H | A | 125-127 | $C_{17}H_{20}N_2O_3$ |
| 24 | 4-methylphenylmethyl | 4-Cl | H | A | 196-197 | $C_{22}H_{21}ClN_2O_2$ |
| 25 | 3-methoxypropyl | 4-Cl | H | B | 164-166.5 | $C_{18}H_{21}ClN_2O_3$ |
| 26 | butyl | 4-Cl | H | A | 192-194.5 | $C_{18}H_{21}ClN_2O_2$ |
| 27 | hexyl | 4-Cl | H | A | 162-164 | $C_{20}H_{25}ClN_2O_2$ |
| 28 | octyl | 4-Cl | H | A | 155-157 | $C_{22}H_{29}ClN_2O_2$ |
| 29 | 4-chlorophenylmethyl | 4-Cl | H | A | 245-246 | $C_{21}H_{18}Cl_2N_2O_2$ |
| 30 | 2,4-dichlorophenylmethyl | 4-Cl | H | A | 236.5-238.5 | $C_{21}H_{17}Cl_3N_2O_2$ |
| 31 | 4-methoxyphenylmethyl | 4-Cl | H | A | 187.5-189 | $C_{22}H_{21}ClN_2O_3$ |
| 32 | 2-furylmethyl | 4-Cl | H | A | 205.5-208 | $C_{19}H_{17}N_2O_3$ |
| 33 | 3-pyridylmethyl | 4-Cl | H | A | 184-187 | $C_{20}H_{18}ClN_3O_2$ |
| 34 | 2-dimethylaminoethyl | 4-Cl | H | B | 162-164 | $C_{18}H_{22}ClN_3O_2$ |
| 35 | 4-chlorophenylmethyl | 3-$CH_3$ | H | A | 187-190.5 | $C_{22}H_{21}ClN_2O_2$ |
| 36 | butyl | 3-$CH_3$ | H | A | 135.5-138 | $C_{19}H_{24}N_2O_2$ |
| 37 | butyl | 3-Cl | H | A | 140-142 | $C_{18}H_{21}ClN_2O_2$ |
| 38 | butyl | 3-$NO_2$ | H | A | 188-192 | $C_{18}H_{22}N_3O_4$ |
| 39 | butyl | 3-$OCH_3$ | H | A | 131-133 | $C_{19}H_{24}N_2O_3$ |
| 40 | butyl | 3-Cl | 4-Cl | A | 174-175.5 | $C_{18}H_{20}Cl_2N_2O_2$ |
| 41 | 4-chlorophenylmethyl | 3-Cl | H | A | 210-212 | $C_{21}H_{18}Cl_2N_2O_2$ |
| 42 | 4-chlorophenylmethyl | 3-Br | H | A | 191-193.5 | $C_{21}H_{18}BrClN_2O_2$ |
| 43 | 4-chlorophenylmethyl | 3-$CF_3$ | H | A | 173-174 | $C_{22}H_{18}ClF_3N_2O_2$ |
| 44 | 4-chlorophenylmethyl | 3-$OCH_3$ | H | A | 180.5-184 | $C_{22}H_{21}ClN_2O_3$ |
| 45 | 4-chlorophenylmethyl | 3-$CH_3$ | 4-$CH_3$ | A | 231-233 | $C_{23}H_{23}ClN_2O_2$ |
| 46 | 4-methylphenylmethyl | 3-$CH_3$ | H | A | 163.5-165 | $C_{23}H_{24}N_2O_2$ |
| 47 | 4-methylphenylmethyl | 3-Cl | H | A | 197-199 | $C_{22}H_{21}ClN_2O_2$ |
| 48 | 4-methylphenylmethyl | 3-Br | H | A | 149.5-151 | $C_{22}H_{21}BrN_2O_2$ |
| 49 | 4-methylphenylmethyl | 3-$CF_3$ | H | A | 168-169 | $C_{23}H_{21}F_3N_2O_2$ |
| 50 | 4-chlorophenylmethyl | 4-$CH_3$ | H | A | 240-243 | $C_{22}H_{21}ClN_2O_2$ |
| 51 | butyl | 4-$CH_3$ | H | A | 210.5-215 | $C_{19}H_{24}N_2O_2$ |
| 52 | 4-chlorophenylmethyl | 4-Et | H | A | 190-196 | $C_{23}H_{23}ClN_2O_2$ |
| 53 | 2-thienylmethyl | H | H | A | 165-167 | $C_{19}H_{18}N_2O_2S$ |
| 54** | 4-methylphenylmethyl | H | H | A | 204-207 | $C_{22}H_{23}ClN_2O_2$ |
| 55 | 2-fluorophenylmethyl | 4-Cl | H | A | 207-210 | $C_{21}H_{18}ClFN_2O_2$ |
| 56 | 2-methylphenylmethyl | 4-Cl | H | A | 258-261 | $C_{22}H_{21}ClN_2O_2$ |
| 57 | butyl | 3-Br | H | A | 142.5-145.5 | $C_{18}H_{21}BrN_2O_2$ |
| 58 | 4-chlorophenylmethyl | 3-Cl | 4-Cl | A | 195-197 | $C_{21}H_{17}Cl_3N_2O_2$ |
| 59 | butyl | 3-$CH_3$ | 4-$CH_3$ | A | 174.8-176.5 | $C_{20}H_{26}N_2O_2$ |
| 60 | butyl | 3-$CF_3$ | H | A | 150-152.5 | $C_{19}H_{21}F_3N_2O_2$ |
| 61 | 4-methylphenylmethyl | 3-$OCH_3$ | H | A | 160-162 | $C_{23}H_{24}N_2O_3$ |
| 62 | butyl | 4-Et | H | A | 169-171 | $C_{20}H_{26}N_2O_3$ |
| 63 | phenylmethyloxy | H | H | A | 179-180.5 | $C_{21}H_{20}N_2O_3$ |

*Compound 20 is a solvate which contains equivalent methanol
**Compound 55 is a hydrochloride.

TABLE 2

| Ex. No. | IR $\nu$ value (cm$^{-1}$) | Method | NMR Chemical shift $\delta$ value | Solvent | Conc. (ppm) | Evaluation Plant. X | Y | Z |
|---|---|---|---|---|---|---|---|---|
| 1 | 1633,1667 | KBr | 2.21(3H),2.77(3H),6.40(1H,5-H) | $CDCl_3$ | 20 | 4 | 4 | 1 |
|   |   |   |   |   | 100 | 4 | 4 | 1 |
| 2 | 1627,1655 | " |   |   | 20 | 4 | 4 | 1 |
|   |   |   |   |   | 100 | 4 | 4 | 1 |
| 3 | 1637,1657 | " | 2.33(3H),2.87(3H),6.34(1H,5-H) | " | 20 | 1 | 3 | 1 |
|   |   |   |   |   | 100 | 1 | 3 | 3 |
| 4 | 1630,1675 | " | 2.32(3H),2.85(3H),6.35(1H,5-H) | " | 20 | 3 | 4 | 1 |
|   |   |   |   |   | 100 | 3 | 4 | 1 |
| 5 | 1623,1657 | " | 2.34(3H),2.87(3H),6.35(1H,5-H) | " | 20 | 4 | 3 | 1 |
|   |   |   |   |   | 100 | 4 | 3 | 1 |
| 6 | 1630,1670 | " | 2.29(3H),2.83(3H),6.36(1H,5-H) | " | 20 | 1 | 1 | 1 |
|   |   |   |   |   | 100 | 1 | 2 | 1 |
| 7 | 1627,1660 | " | 2.20(3H),2.77(3H),6.44(1H,5-H) | " | 20 | 4 | 4 | 1 |
|   |   |   |   |   | 100 | 4 | 4 | 1 |
| 8 | 1627,1665 | " | 2.20(3H),2.77(3H),6.44(1H,5-H) | " | 20 | 4 | 4 | 1 |
|   |   |   |   |   | 100 | 4 | 4 | 1 |
| 9 | 1630,1673 | " | 2.23(3H),2.79(3H),6.42(1H,5-H) | " | 20 | 4 | 4 | 2 |
|   |   |   |   |   | 100 | 4 | 4 | 2 |
| 10 | 1625,1650 | " |   |   | 20 | 4 | 4 | 1 |
|   |   |   |   |   | 100 | 4 | 4 | 1 |
| 11 | 1627,1657 | " | 2.23(3H),2.33(3H),6.26(1H,5-H) | DMSO-$d_6$ | 20 | 4 | 4 | 1 |
|   |   |   |   |   | 100 | 4 | 4 | 1 |
| 12 | 1625,1660 | " | 2.28(3H),2.86(3H),3.88(3H),6.50(1H,5-H) | $CDCl_3$ | 20 | 3 | 4 | 1 |
|   |   |   |   |   | 100 | 4 | 4 | 1 |
| 13 | 1600,1630,1673 | " | 2.24(3H),2.80(3H),3.70(3H),6.39(1H,5-H) | " | 20 | 4 | 4 | 1 |

TABLE 2-continued

| Ex. No. | IR ν value (cm⁻¹) | Method | NMR Chemical shift δ value | Solvent | Conc. (ppm) | Evaluation Plant. X | Y | Z |
|---|---|---|---|---|---|---|---|---|
| 14 | 1620,1660 | " | 2.28(3H),2.83(3H),3.73(3H),6.43(1H,5-H) | " | 100<br>20 | 4<br>4 | 4<br>4 | 1<br>1 |
| 15 | 1633,1675 | " | 2.24(3H),2.29(3H),2.80(3H),6.42(1H,5-H) | " | 100<br>20 | 4<br>4 | 4<br>4 | 1<br>3 |
| 16 | 1627,1665 | " | 2.23(3H),2.30(3H),2.80(3H),6.41(1H,5-H) | " | 100<br>20 | 4<br>4 | 4<br>4 | 2<br>2 |
| 17 | 1623,1660 | " | 2.26(3H),2.80(3H),6.41(1H,5-H) | " | 100<br>20 | 3<br>3 | 4<br>4 | 1<br>1 |
| 18 | 1623,1655 | " | 1.35(9H),2.29(3H),2.83(3H),6.46(1H,5-H) | " | 100<br>20 | 2<br>2 | 2<br>2 | 1<br>1 |
| 19 | — | " | 2.40(3H),2.93(3H),6.35(1H,5-H) | " | 100<br>20 | 1<br>2 | 3<br>4 | 1<br>1 |
| 20 | — | " | 2.28(3H),2.79(3H),6.42(1H,5-H) | " | 100<br>20 | 3<br>4 | 4<br>4 | 1<br>1 |
| 21 | 1627,1660 | " | 2.23(3H),2.80(3H),6.41(1H,5-H) | " | 100<br>20 | 1<br>1 | 1<br>3 | 1<br>1 |
| 22 | 1625,1673 | " | 2.31(3H),2.83(3H),6.48(1H,5-H) | " | 100<br>20 | 4<br>4 | 4<br>4 | 1<br>1 |
| 23 | 1600,1620,1657 | " | 2.38(3H),2.88(3H),3.27(3H),6.32(1H,5-H) | " | 100<br>20 | 1<br>1 | 2<br>3 | 1<br>1 |
| 24 | 1625,1660 | " | | | 100<br>20 | 3<br>3 | 3<br>3 | 1<br>1 |
| 25 | 1630,1667 | " | 2.37(3H),2.89(3H),3.29(3H),6.34(1H,5-H) | " | 100<br>20 | 3<br>3 | 3<br>4 | 3<br>4 |
| 26 | 1605,1625,1657 | " | 2.33(3H),2.85(3H),6.33(1H,5-H) | " | 100<br>20 | 1<br>2 | 1<br>3 | 2<br>4 |
| 27 | 1625,1673 | " | 2.35(3H),2.88(3H),6.35(1H,5-H) | " | 100<br>20 | 1<br>1 | 4<br>4 | 1<br>2 |
| 28 | 1603,1617,1663 | " | 2.33(3H),2.87(3H),6.32(1H,5-H) | " | 100<br>20 | 1<br>1 | 2<br>3 | 1<br>1 |
| 29 | 1627,1663 | " | | | 100<br>20 | 1<br>1 | 4<br>4 | 1<br>3 |
| 30 | 1627,1657 | " | | | 100<br>20 | 1<br>1 | 3<br>3 | 1<br>1 |
| 31 | 1633,1680 | " | 2.28(3H),2.82(3H),3.73(3H),6.42(1H,5-H) | " | 100<br>20 | 1<br>1 | 1<br>2 | 2<br>2 |
| 32 | 1610,1633,1667 | " | | | 100<br>20 | 1<br>1 | 1<br>1 | 1<br>1 |
| 33 | 1627,1670 | " | 2.28(3H),2.81(3H),6.44(1H,5-H) | " | 100<br>20 | 1<br>1 | 1<br>2 | 2<br>3 |
| 34 | 1635,1675 | " | 2.27(6H),2.35(3H),2.90(3H),6.32(1H,5-H) | " | 100<br>20 | 1<br>1 | 1<br>2 | 2<br>2 |
| 35 | 1610,1627,1663 | " | | | 100<br>20 | 5<br>5 | 4<br>4 | 1<br>1 |
| 36 | | | 2.30(6H),2.86(3H),6.31(1H,5-H) | " | 100<br>20 | 1<br>1 | 1<br>4 | 3<br>4 |
| 37 | 1640,1667 | " | 2.35(3H),2.88(3H),6.33(1H,5-H) | " | 100<br>20 | 1<br>2 | 1<br>3 | 4<br>4 |
| 38 | 1603,1633,1673 | " | 2.40(3H),2.91(3H),6.38(1H,5-H) | " | 100<br>20 | 4<br>5 | 4<br>4 | 4<br>4 |
| 39 | 1627,1667 | " | 2.32(3H),2.85(3H),3.73(3H),6.30(1H,5-H) | " | 100<br>20 | 1<br>1 | 1<br>2 | 3<br>4 |
| 40 | 1633,1675 | " | 2.36(3H),2.88(3H),6.36(1H,5-H) | " | 100<br>20 | 1<br>1 | 1<br>2 | 1<br>4 |
| 41 | 1630,1665 | " | | | 100<br>20 | 1<br>1 | 4<br>4 | 1<br>1 |
| 42 | 1627,1660 | " | | | 100<br>20 | 1<br>1 | 2<br>2 | 2<br>3 |
| 43 | 1617,1670 | " | 2.29(3H),2.84(3H),6.46(1H,5-H) | " | 100<br>20 | 1<br>1 | 1<br>2 | 2<br>2 |
| 44 | 1630,1665 | " | | | 100<br>20 | 1<br>1 | 1<br>4 | 1<br>1 |
| 45 | 1627,1660 | " | | | 100<br>20 | 1<br>1 | 2<br>2 | 1<br>1 |
| 46 | 1630,1667 | " | | | 100<br>20 | 4<br>4 | 4<br>4 | 1<br>1 |
| 47 | 1623,1665 | " | | | 100<br>20 | 1<br>1 | 4<br>4 | 1<br>1 |
| 48 | 1623,1677 | " | | | 100<br>20 | 1<br>1 | 3<br>3 | 1<br>2 |
| 49 | 1627,1665 | " | 2.31(3H),2.32(3H),2.87(3H),6.48(1H,5-H) | " | 100<br>20 | 1<br>1 | 1<br>2 | 2<br>2 |
| 50 | 1627,1665 | " | | | 100<br>20 | 1<br>1 | 4<br>4 | 1<br>1 |
| 51 | 1603,1627,1657 | " | 2.27(3H),2.32(3H),2.87(3H),6.32(1H,5-H) | " | 100<br>20 | 1<br>1 | 2<br>2 | 4<br>4 |
| 52 | 1633,1665 | " | | | 20 | 1 | 1 | 1 |

TABLE 2-continued

| Ex. No. | IR ν value (cm$^{-1}$) | NMR Method | Chemical shift δ value | Solvent | Conc. (ppm) | Plant. X | Y | Z |
|---|---|---|---|---|---|---|---|---|
| 53 | 1627,1665 | " | 2.34(3H),2.90(3H),6.39(1H,5-H) | " | 100 | 2 | 1 | 1 |
|    |           |   |                               |   | 20  | 3 | 4 | 1 |
|    |           |   |                               |   | 100 | 3 | 4 | 1 |
| 54 | 1617,1675 | " |                               |   | 20  | 4 | 4 | 1 |
|    |           |   |                               |   | 100 | 4 | 4 | 1 |
| 55 | 1633,1673 | " | 2.26(3H),2.80(3H),6.40(1H,5-H) | " | 20  | 1 | 3 | 1 |
|    |           |   |                               |   | 100 | 1 | 3 | 3 |
| 56 | 1603,1623,1660 | " |                          |   | 20  | 1 | 1 | 1 |
|    |           |   |                               |   | 100 | 1 | 2 | 1 |
| 57 | 1640,1665 | " | 2.31(3H),2.84(3H),6.32(1H,5-H) | " | 20  | 1 | 2 | 3 |
|    |           |   |                               |   | 100 | 3 | 3 | 4 |
| 58 | 1625,1660 | " | 2.25(3H),2.78(3H),6.41(1H,5-H) | " | 20  | 1 | 1 | 1 |
|    |           |   |                               |   | 100 | 1 | 3 | 1 |
| 59 | 1627,1633 | " | 2.23(6H),2.36(3H),2.90(3H), 6.37(1H,5-H) | " | 20 | 4 | 5 | 4 |
|    |           |   |                               |   | 100 | 4 | 5 | 4 |
| 60 | 1610,1643,1667 | " | 2.37(3H),2.91(3H),6.34(1H,5-H) | " | 20 | 1 | 2 | 3 |
|    |           |   |                               |   | 100 | 2 | 3 | 4 |
| 61 | 1603,1607, 1660,1675 | " |                       |   | 20  | 1 | 4 | 2 |
|    |           |   |                               |   | 100 | 2 | 4 | 2 |
| 62 | 1627,1660 | " | 2.34(3H),2.90(3H),6.30(1H,5-H) | " | 20  | 1 | 1 | 1 |
|    |           |   |                               |   | 100 | 1 | 1 | 1 |
| 63 | 1627,1660 | " | 2.38(3H),3.03(3H),6.33(1H,5-H) | " | 20  | 2 | 3 | 2 |
|    |           |   |                               |   | 100 | 3 | 3 | 3 |

X: *Oryza sativa* L.
Y: *Echinochloa crus-galli* L.
Z: *Raphanus sativus* L.

What we claim is:

1. A method for inhibiting plant growth comprising treating the plant or its seed with a plant growth inhibitory-effective amount of a compound of the formula (I):

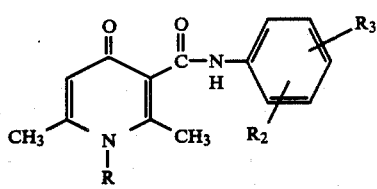

or a salt thereof wherein R is an alkoxy group, an aralkyloxy group selected from the group consisting of phenylmethoxy, phenethyloxy, phenylpropoxy, or phenylbutoxy, which may be substituted on the aryl ring by an alkyl or a halogen atom, or a group of —(CH$_2$)$_n$—R$_1$ wherein n is an integer from 1 to 3 and R$_1$ is a hydroxy group, lower alkoxy group, mercapto group, lower alkylthio group, amino group, di-lower alkylamino group, C$_{3-11}$ alkyl group, lower alkenyl group, lower alkynyl group, cycloalkyl group, a furyl or pyridyl group which may be substituted by halogen, lower alkyl, or phenyl, or a phenyl or naphthyl group substituted by one or two substituents of halogen, lower alkyl, or lower alkoxy; R$_2$ and R$_3$ bond at the 3, 4, or 5 position on the benzene ring and are, the same or different, a hydrogen atom, halogen atom, cyano group, nitro group, amino group, lower alkyl group, halogenated lower alkyl group, hydroxy group, lower alkoxy group, carboxy, lower alkoxycarbonyl group, or a phenyloxy group or naphthyloxy group which may be substituted on the aryl ring by a halogen atom, a lower alkyl group and/or a lower alkoxy group.

2. A method for inhibiting plant growth comprising treating the plant or its seed with a plant growth inhibitory-effective amount of a compound of claim 1 wherein the lower alkyl, lower alkenyl, lower alkynyl, or lower alkoxy group in R$_1$, R$_2$ and R$_3$ of the formula (I) compound has from 1 to 5 carbon atoms.

3. A method for inhibiting plant growth comprising treating the plant or its seed with a plant growth inhibitory-effective amount of a compound of claim 1 wherein the halogen atom in R$_1$, R$_2$ and R$_3$ of the formula (I) compound is chlorine, bromine, or fluorine.

4. A method for inhibiting plant growth comprising treating the plant or its seed with a plant growth inhibitory-effective amount of a compound of claim 1 wherein R$_1$ is phenyl and R$_2$ and R$_3$ are phenyloxy.

5. A method for inhibiting plant growth comprising treating the plant or its seed with a plant growth inhibitory-effective amount of a compound of claim 1 wherein the heterocyclic group in R$_1$ of the formula (I) compound is a furyl or pyridyl group.

6. A method for inhibiting plant growth comprising treating the plant or its seed with a plant growth inhibitory-effective amount of a compound of claim 1 wherein

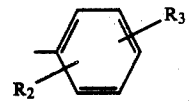

in the formula (I) compound is a 3-methylphenyl or 3- or 4-chlorophenyl group.

7. A method for inhibiting plant growth comprising treating the plant or its seed with a plant growth inhibitory-effective amount of a compound of claim 1 wherein the —(CH$_2$)$_n$—R$_1$ group in the formula (I) compound is a 4-fluorophenylmethyl, 4-chlorophenylmethyl, or 4-methylphenylmethyl group.

8. A method for inhibiting plant growth comprising treating the plant or its seed with a plant growth inhibitory-effective amount of a compound of claim 1 selected from the group consisting of 1-(4-fluorophenylmethyl)-1,4-dihydro-2,6-dimethyl-4-oxo-N-phenyl-3-pyridinecarboxamide, 1-(4-chlorophenylmethyl)-1,4-dihydro-2,6-dimethyl-4-oxo-N-phenyl-3-pyridinecarboxamide,
1-(3-chlorophenylmethyl)-1,4-dihydro-2,6-dimethyl-4-oxo-N-phenyl-3-pyridinecarboxamide,
1,4-dihydro-2,6-dimethyl-1-(3-methylphenylmethyl)-4-oxo-N-phenyl-3-pyridinecarboxamide,
1,4-dihydro-2,6-dimethyl-1-(4-methylphenylmethyl)-4-oxo-N-phenyl-3-pyridinecarboxamide,
N-(4-chlorophenyl)-1,4-dihydro-2,6-dimethyl-1-(4-methylphenylmethyl)-4-oxo-3-pyridinecarboxamide,
N-(4-chlorophenyl)-1-(4-chlorophenylmethyl)-1,4-dihydro-2,6-dimethyl-4-oxo-3-pyridinecarboxamide,
1-(4-chlorophenylmethyl)-1,4-dihydro-2,6-dimethyl-N-(3-methylphenyl)-4-oxo-3-pyridinecarboxamide,
1-(4-chlorophenylmethyl)-1,4-dihydro-2,6-dimethyl-N-(4-methylphenyl)-4-oxo-3-pyridinecarboxamide,
1,4-dihydro-2,6-dimethyl-N-(3-methylphenyl)-1-(4-methylphenylmethyl)-4-oxo-3-pyridinecarboxamide,
N-(3-chlorophenyl)-1-(4-chlorophenylmethyl)-1,4-dihydro-2,6-dimethyl-4-oxo-3-pyridinecarboxamide,
N-(3-chlorophenyl)-1,4-dihydro-2,6-dimethyl-1-(4-methylphenylmethyl)-4-oxo-3-pyridinecarboxamide,
and salts thereof.

* * * * *